United States Patent [19]

Deschler et al.

[11] Patent Number: 4,623,740

[45] Date of Patent: Nov. 18, 1986

[54] N,N'- AND N,N',N'-SUBSTITUTED SILYLUREAS AND PROCESS FOR THEIR PRODUCTION

[76] Inventors: Ulrich Deschler, Birkenweg 1, D-6450 Hanau 9, Fed. Rep. of Germany; Wolfgang Buder, Rua do Lagarto Azul No. 1000, 40.000 Salvador/Bahia, Brazil; Peter Kleinschmit, Wildaustrasse 19, D-6450 Hanau 9; Rudolf Michel, Josefstrasse 36, D-6463 Freigericht, both of Fed. Rep. of Germany

[21] Appl. No.: 750,272

[22] Filed: Jul. 1, 1985

[30] Foreign Application Priority Data

Jul. 4, 1984 [DE] Fed. Rep. of Germany ....... 3424534

[51] Int. Cl.$^4$ .............................................. C07F 7/10
[52] U.S. Cl. .................................... 556/421; 556/416; 556/417; 544/39; 544/159; 544/386; 548/110
[58] Field of Search ...................... 556/421, 417, 416; 544/39, 159, 386; 548/110

[56] References Cited

U.S. PATENT DOCUMENTS

| 3,208,971 | 9/1965 | Gilkey et al. | 556/421 X |
| 3,493,461 | 2/1970 | Sterman et al. | 161/193 |
| 4,046,794 | 9/1977 | Pepe et al. | 556/421 |
| 4,234,573 | 11/1980 | Böger et al. | 556/421 X |
| 4,271,229 | 6/1981 | Temple | 428/288 |

FOREIGN PATENT DOCUMENTS

| 0665127 | 6/1963 | Canada | 556/421 |
| 77036 | 4/1983 | European Pat. Off. | 556/421 X |
| 56-57792 | 7/1981 | Japan | 556/421 X |
| 57-16892 | 1/1982 | Japan | 556/421 |

OTHER PUBLICATIONS

Chem. Abst., vol. 95, item 204, 144 (1981).

Primary Examiner—Paul F. Shaver
Attorney, Agent, or Firm—Cushman, Darby & Cushman

[57] ABSTRACT

The invention is directed to N,N' and N,N',N'-substituted silylureas and a process for their production in which in a single step process there are reacted a halogenoalkylsilane or a halogenbenzylsilane with a primary or secondary amine and an alkali cyanate in equimolar amounts.

15 Claims, No Drawings

N,N'- AND N,N',N'-SUBSTITUTED SILYLUREAS AND PROCESS FOR THEIR PRODUCTION

BACKGROUND OF THE INVENTION

The invention is directed to N,N' and N,N',N'-substituted silylureas and a process for their production.

N-substituted silylureas have been known for a long time and are employed as adhesive agents for coating glass fibers (Temple U.S. Pat. No. 4,271,229, European published application No. 77,036).

However, there have only been described a few N,N' and only one N,N',N'-substituted silylureas. These also are used in the above-mentioned areas.

Netherlands patent application No. 8006415 is directed to coating glass fibers with polyurethane dispersions, which contains as functional silyureas γ-methylureidopropyltriethoxysilane or γ-dimethylureidopropyltriethoxysilane. The exact positions of the methyl groups are not clear. A mechanism of the process for the production of N'N'-dimethyl-3-trimethoxysilylpropylurea can be inferred from Pepe U.S. Pat. No. 4,046,794. According to this, 3-isocyanatopropyltrialkoxysilane is reacted with dimethylamine.

According to Japan published application No. 8157792 (Chem. Abst. Vol. 95:204144 w (1981)), there are obtained N'-cyclohexyl- or N'-phenyl-substituted silylureas by treating 3-aminopropyl silanes with phenyl or cyclohexylisocyanate.

There is described in Sterman U.S. Pat. No. 3,493,461 a N,N'-bis-3-trimethoxysilylpropylurea; however, a process for its production is not disclosed.

These compounds are used in the treatment of glass fibers which are to be worked into polyvinyl chloride.

The problem of the invention is to make N'N'- and N,N',N'-substituted silyl functional ureas and develop a simple process for their production.

SUMMARY OF THE INVENTION

The invention is directed to N,N'- and N''N',N'-substituted silylureas of the formula (I)

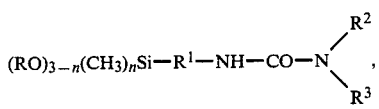

where
n is 0 or 1
R is $C_1-C_6$ alkyl, phenyl, $C_5-C_8$ cycloalkyl
$R^1$ is $-(CH_2)_3-$,

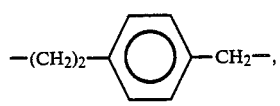

$R^2$, $R^3$ are
- $C_1-C_{18}$ alkyl,
- $C_5-C_8$ cycloalkyl,
- $C_1-C_3$ alkyl, terminally substituted by an amino-, thio- or cyano group,
- $-(C_2H_4NH)_mH$ where m is 2 or 3,
- $C_3-C_{18}$ alkenyl,

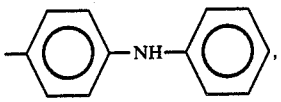

benzyl, phenyl, naphthyl, pyridyl, triazyl or such a group having at least one substituent which is an amino, hydroxyl, thio, $C_1-C_3$ alkoxy, nitro, or carboxyl group or a silyl group of the formula $(RO)_{3-n}(CH_3)_n Si-R^4-$ in which $R^4$ is $C_1-C_3$ alkylene,

or $R^2$ and $R^3$ together with the nitrogen atom and 0, 1, or 2 further heteroatoms forms a monovalent 5 to 14 numbered saturated or unsaturated cyclic group having 2 to 12 carbon atoms, with the proviso that $R^2$ can also be hydrogen and with the further proviso there are excluded:

1. $(C_2H_5O)_2R^6Si(CH_2)_3-NH-CO-NHR^5$ where $R^5$ is cyclohexyl and $R^6$ is methyl or $R^5$ is phenyl and $R^6$ is ethoxy and
2. $(CH_3O)_3Si(CH_2)_3-NH-CO-NH-(CH_2)_3-Si(OC_2H_5)_3$ and
3.

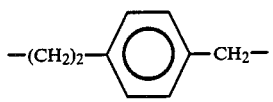

where $R^7$ is $CH_3$ or H.

Any alkyl or alkenyl group can be linear or branched and $R^2$ and $R^3$ can be the same or different.

A further object of the invention is the development of a process for the production of the new compounds as well as the known compounds which is carried out in one step, leads to high yields of product, and without isolating the intermediate silylalkylisocyanate according to the state of the art.

The desired compounds are produced in excellent yields according to the process of the invention.

The process for producing the compounds comprising first adding to a solution of an amino compound of the formula (III)

where $R^2$ and $R^3$ are as defined above, in an aprotic, polar, organic solvent an equimolar amount of alkali cyanate and subsequently adding an equimolar amount of a halosilane of the formula IV $(RO)_{3-n}(CH_3)_n Si-R^1-X,$ where R, $R^1$ and n are as defined above and X=Cl, Br, or I, heating to 120° to 155° C., stirring for 1 to 8 hours at 130° to 150° C., preferably 4 hours at 140° C. and separating the product after the resulting reaction. Mixing of amine and cyanate takes place at room temperature within 1 to 20 minutes depending on their amounts.

The new process consequently can be used with the compounds that are not included within the scope of the novel compounds.

As solvents there are especially suited dimethylformamide (DMF) and dimethylsulfoxide (DMSO).

As amines of formula (III), there are preferably employed: di and monoalkylamines having straight or branched alkyl chains and having up to 18 carbon atoms, e.g., methylamine, dimethylamine, butylamine dibutylamine, sec. butylamine, octadecylamine, dioctadecylamine, ethylenediamine, diethylenetriamine, triethylenetetramine, diallylamine, allylamine, 3-aminophenol, 2-mercaptoaniline, benzylamine, 4-methoxyaniline, 4-nitroaniline, 4-aminodiphenylamine, 1,8-naphthalenediamine, diphenylamine, 1-naphthylphenylamine, 2-naphthylphenylamine, N-isopropyl-N'-phenyl-p-phenylendiamine, N-(1,3-dimethylbutyl)-N-phenyl-p-phenylenediamine N,N'-bis(1,4-dimethylpentyl)p-phenylendiamine, imidazole, pyrazole, 1,2,3-triazole, 1,2,4-triazole, piperazine, pyrazoline, imidazolidine, morpholine, triazolidine, indazole, azimidobenzene, benzimidazole, indole, phenothiazine.

Other suitable amines include octadecenylamine, cyclopentylamine, cyclohexylamine, cyclooctylamine, 4-propoxyaniline.

As aminosilyl compounds, there are preferably employed trialkoxy compounds especially 3-aminopropyltriethoxysilane and 3-aminopropyltrimethoxysilane, bis(-3-triethoxysilylpropyl)amine, bis(-3-trimethoxysilylpropyl)amine or 3-aminopropylmethyldiethoxysilane and 3-aminopropylmethyldimethoxysilane.

Other suitable silane compounds include 3-aminopropyltrihexoxylsilane, 3-aminopropyltrisphenoxysilane, 3-aminopropyldimethoxyphenoxysilane, 3-aminopropylcyclopentoxydiethoxysilane, 3-aminopropyltricyclohexoxysilane, 3-aminopropyldiethoxycyclooctylsilane.

In order to avoid transesterification during the reaction, preferably there is reacted an aminosilane compound of formula (III) only with the halo compounds of formula (IV) which have the same alkoxy-, cycloalkoxy-, or aryloxy groups.

As alkali cyanate, there is especially employed potassium cyanate. There can also be used, for example, sodium cyanate.

The amount of solvent is 250 to 400, preferably 300 ml, per mole of amine. If the viscosity of the reaction mixture increases strongly during the reaction, there is dosed in more solvent. After the completion of the reaction, the mixture is allowed to cool to room temperature, the precipitated salt is filtered off, and the desired compound is isolated after removing the solvent with suction. Low boiling compounds may be purified by vacuum distillation.

There are produced in the example portion of the specification compounds of formula (I) using the process of the invention and which are regarded as being confirmed by the data of the corresponding analytical values. The analytical values are arranged in a separate table with the corresponding example numbers. As solvents in the experiments, there were used dimethylformamide and dimethylsulfoxide.

The process can comprise, consist essentially of, or consist of the stated steps with the recited reactants.

The entire disclosure of German priority application P3424534.0 is hereby incorporated by reference.

EXAMPLE 0.75 mole of trismethoxysilyl-3-chloropropane is reacted with 0.75 mole of ethylenediamine and 0.75 mole of potassium cyanate in 200 ml of dimethylformamide at 140° C. for 4 hours.

The mixture of the diamine and the cyanate was prepared by adding the cyanate to the solution of the diamine in dimethylformamide at room temperature within 5 minutes. After the completion of the reaction, the reaction mixture is allowed to cool to room temperature, the precipitated potassium chloride is filtered off and 194.8 grams of $(CH_3O)_3Si-C_3H_6-NH-CO-NH-C_2H_4-NH_2$ were isolated after removing the solvent with suction.

The other desired compounds were prepared following this scheme.

| Example | Silane Employed | Amount [mole] | Amine | Amount [mole] | Product | Amount [gram] |
|---|---|---|---|---|---|---|
| 1 | (CH₃O)₃Si—C₃H₆—Cl | 0,75 | H₂N—C₂H₄—NH₂ | 0,75 | (CH₃O)₃Si—C₃H₆—NH—CO—NH—C₂H₄—NH₂ | 194,8 |
| 2 | (C₂H₅O)₃Si—C₃H₆—Cl | 0,75 | H₂N—C₂H₄—NH₂ | 0,75 | (C₂H₅O)₃Si—C₃H₆—NH—CO—NH—C₂H₄—NH₂ | 209,7 |
| 3 | (C₃H₇O)₃Si—C₃H₆—Cl | 0,5 | H₂N—C₆H₄—NH—C₆H₅ | 0,5 | (C₃H₇O)₃Si—C₃H₆—NH—CO—NH—C₆H₄—NH—C₆H₅ | 227,6 |
| 4 | (CH₃O)₂Si(CH₃)—C₃H₆—Cl | 0,5 | HN(C₆H₅)₂ | 0,5 | (CH₃O)₂Si(CH₃)—C₃H₆—NH—CO—N(C₆H₅)₂ | 148,5 |
| 5 | (CH₃O)₃Si—C₂H₄—C₆H₄—CH₂—Cl | 0,25 | H₂N—C₂H₄—NH₂ | 0,25 | (CH₃O)₃Si—C₂H₄—C₆H₄—CH₂—NH—CO—NH—C₂H₄—NH₂ | 84,6 g |
| 6 | (CH₃O)₃Si—C₃H₆—Br | 0,5 | H₂N—C₆H₄—NH—C₆H₅ | 0,5 | (CH₃O)₃Si—C₃H₆—NH—CO—NH—C₆H₄—NH—C₆H₅ | 193,8 |
| 7 | (C₂H₅O)₃Si—C₃H₆—J | 0,5 | HN(C₆H₅)₂ | 0,5 | (C₂H₅O)₃Si—C₃H₆—NH—CO—N(C₆H₅)₂ | 173,2 |
| 8 | (CH₃O)₃Si—C₃H₆—Cl | 0,75 | H₂N—C₈H₁₇ | 0,75 | (CH₃O)₃Si—C₃H₆—NH—CO—NH—C₈H₁₇ | 246,8 |
| 9 | (CH₃O)₃Si—C₃H₆—Cl | 1,00 | H₂N—C₁₈H₃₇ | 1,00 | (CH₃O)₃Si—C₃H₆—NH—CO—NH—C₁₈H₃₇ | 439,4 |
| 10 | (CH₃O)₃Si—C₃H₆—Cl | 0,5 | H₂N—C₈H₁₆—CH=CH—C₈H₁₇ | 0,5 | (CH₃O)₃Si—C₃H₆—NH—CO—NH—C₈H₁₆—CH=CH—C₈H₁₇ | 217,6 |
| 11 | (CH₃O)₃Si—C₃H₆—Cl | 0,5 | H₂N—C₂H₄(—NH—C₂H₄)₂—NH₂ | 0,5 | (CH₃O)₃Si—C₃H₆—NH—CO—(NH—C₂H₄—)₃NH₂ | 174,0 |
| 12 | (C₂H₅O)₃Si—C₃H₆—Cl | 0,5 | H₂N—C₃H₆—Si(OC₂H₅)₃ | 0,5 | (C₂H₅O)₃Si—C₃H₆—NH—CO—NH—C₃H₆—Si(OC₂H₅)₃ | 198,7 |
| 13 | (CH₃O)₃Si—C₃H₆—Cl | 0,5 | H₂N—C₂H₄—N(C₂H₅)₂ | 0,5 | (CH₃O)₃Si—C₃H₆—NH—CO—NH—C₂H₄—N(C₂H₅)₂ | 141,4 |
| 14 | (CH₃O)₃Si—C₃H₆—Cl | 0,11 | H₂N—⟨triazine-dithiol⟩ | 0,11 | (CH₃O)₃Si—C₃H₆—NH—CO—NH—⟨triazine-dithiol⟩ | 40,8 |
| 15 | (C₂H₅O)₃Si—C₃H₆—Cl | 0,5 | HN(C₄H₉)₂ | 0,5 | (C₂H₅O)₃Si—C₃H₆—NH—CO—N(C₄H₉)₂ | 177,4 |
| 16 | (CH₃O)₃Si—C₃H₆—Cl | 0,5 | HN(CH₂—CH=CH₂)₂ | 0,5 | (CH₃O)₃Si—C₃H₆—NH—CO—N(CH₂—CH=CH₂)₂ | 141,8 |
| 17 | (CH₃O)₃Si—C₃H₆—Cl | 0,5 | HN(CH₂—CN)₂ | 0,5 | (CH₃O)₃Si—C₃H₆—NH—CO—N(CH₂—CN)₂ | 149,4 |
| 18 | (C₂H₅O)₃Si—C₃H₆—Cl | 0,5 | HN(C₃H₆—Si(OC₂H₅)₃)₂ | 0,5 | (C₂H₅O)₃Si—C₃H₆—NH—CO—N(C₃H₆—Si(OC₂H₅)₃)₂ | 314,9 |
| 19 | (CH₃O)₃Si—C₃H₆—Cl | 1,0 | H₂N—CH₂—C₆H₅ | 1,0 | (CH₃O)₃Si—C₃H₆—NH—CO—NH—CH₂—C₆H₅ | 304,8 |
| 20 | (CH₃O)₃Si—C₃H₆—Cl | 1,5 | H₂N—C₆H₄—NH—C₆H₅ | 1,5 | (CH₃O)₃Si—C₃H₆—NH—CO—NH—C₆H₄—NH—C₆H₅ | 487,8 |

-continued

| Example | Silane Employed | Amount [mole] | Amine | Amount [mole] | Product | Amount [gram] |
|---|---|---|---|---|---|---|
| 21 | (CH₃O)₃Si—C₃H₆—Cl | 0,5 | 1,8-diaminonaphthalene (NH₂, NH₂) | 0,5 | (CH₃O)₃Si—C₃H₆—NH—CO—NH—(naphthyl-NH₂) | 163,7 |
| 22 | (CH₃O)₃Si—C₃H₆—Cl | 0,5 | 3-aminopyridine | 0,5 | (CH₃O)₃Si—C₃H₆—NH—CO—NH—(pyridyl) | 132,5 |
| 23 | (CH₃O)₃Si—C₃H₆—Cl | 0,5 | 3-aminophenol | 0,5 | (CH₃O)₃Si—C₃H₆—NH—CO—NH—(C₆H₄—OH) | 150,3 |
| 24 | (CH₃O)₃Si—C₃H₆—Cl | 0,5 | 2-aminothiophenol | 0,5 | (CH₃O)₃Si—C₃H₆—NH—CO—NH—(C₆H₄—SH) | 144,7 |
| 25 | (CH₃O)₃Si—C₃H₆—Cl | 0,5 | 4-methoxyaniline | 0,5 | (CH₃O)₃Si—C₃H₆—NH—CO—NH—(C₆H₄—OCH₃) | 154,2 |
| 26 | (CH₃O)₃Si—C₃H₆—Cl | 0,5 | 4-nitroaniline | 0,5 | (CH₃O)₃Si—C₃H₆—NH—CO—NH—(C₆H₄—NO₂) | 137,9 |
| 27 | (CH₃O)₃Si—C₃H₆—Cl | 0,5 | HN(C₆H₄—NH—C₆H₅)(CH(CH₃)—CH₂—CH(CH₃)₂) | 0,5 | (CH₃O)₃Si—C₃H₆—NH—CO—N(C₆H₄—NH—C₆H₅)(H₃C—CH—CH₂—CH(CH₃)₂) | 233,8 |
| 28 | (CH₃O)₃Si—C₃H₆—Cl | 0,5 | HN(C₆H₅)₂ | 0,5 | (CH₃O)₃Si—C₃H₆—NH—CO—N(C₆H₅)₂ | 154,9 |

| Example | Silane Employed | Amount [mole] | Amine | Amount [mole] | Product | Amount [gram] |
|---|---|---|---|---|---|---|
| 29 | $(CH_3O)_3Si-C_3H_6-Cl$ | 0,5 | 2-(phenylamino)naphthalene (HN(C$_6$H$_5$)-naphthyl) | 0,5 | $(CH_3O)_3Si-C_3H_6-NH-CO-N(C_6H_5)(\text{naphthyl})$ | 207,2 |
| 30 | $(CH_3O)_3Si-C_3H_6-Cl$ | 0,75 | morpholine | 0,75 | $(CH_3O)_3Si-C_3H_6-NH-CO-N(\text{morpholinyl})$ | 210,2 |
| 31 | $(CH_3O)_3Si-C_3H_6-Cl$ | 0,5 | piperazine | 0,5 | $(CH_3O)_3Si-C_3H_6-NH-CO-N(\text{piperazinyl})$ | 105,4 |
| 32 | $(CH_3O)_3Si-C_3H_6-Cl$ | 1,5 | 1-phenyl-2-(phenylhydrazo) (C$_6$H$_5$-N=N-NH-C$_6$H$_5$) | 1,5 | $(CH_3O)_3Si-C_3H_6-NH-CO-N(-N=N-C_6H_5)(C_6H_5)$ | 446,6 |
| 33 | $(CH_3O)_3Si-C_3H_6-Cl$ | 0,5 | benzimidazole | 0,5 | $(CH_3O)_3Si-C_3H_6-NH-CO-N(\text{benzimidazolyl})$ | 160,1 |
| 34 | $(CH_3O)_3Si-C_3H_6-Cl$ | 0,5 | indole | 0,5 | $(CH_3O)_3Si-C_3H_6-NH-CO-N(\text{indolyl})$ | 145,8 |

-continued
| Example | Silane Employed | Amount [mole] | Amine | Amount [mole] | Product | Amount [gram] |
|---|---|---|---|---|---|---|
| 35 | $(CH_3O)_3Si-C_3H_6-Cl$ | 0.5 | 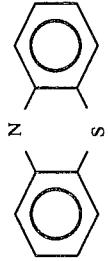 | 0.5 | 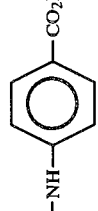 | 202.9 |
| 36 | $(CH_3O)_3Si-C_3H_6-Cl$ | 0.75 | 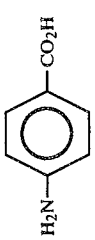 | 0.75 | 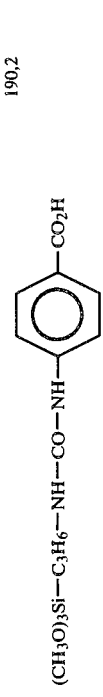 | 190.2 |

| Example | Yield in % | Analyses Calculated Found | | | Remarks |
|---|---|---|---|---|---|
| | | % C | % H | % N | |
| 1 | 97,8 | 40,73 | 8,73 | 15,83 | 200 ml DMF |
| | | 39,21 | 8,15 | 13,65 | |
| 2 | 90,9 | 46,88 | 9,50 | 13,66 | 200 ml DMF |
| | | 46,66 | 9,48 | 11,91 | |
| 3 | 96,1 | 63,39 | 8,30 | 8,87 | Employed NaOCN |
| | | 62,87 | 8,13 | 8,50 | |
| 4 | 82,8 | 63,65 | 7,31 | 7,81 | 150 ml DMF |
| | | 64,59 | 8,12 | 8,48 | |
| 5 | 99,2 | 52,76 | 7,97 | 12,31 | 100 ml DMF |
| | | 52,58 | 7,19 | 10,40 | |
| 6 | 99,5 | 58,58 | 6,98 | 10,78 | 150 ml DMF |
| | | 57,08 | 6,93 | 11,08 | |
| 7 | 83,2 | 63,43 | 7,74 | 6,72 | Employed NaOCN |
| | | 63,58 | 8,11 | 6,81 | |
| 8 | 98,4 | 53,85 | 10,24 | 8,37 | 200 ml DMF |
| | | 52,94 | 10,97 | 8,34 | |
| 9 | 92,5 | 63,24 | 11,46 | 5,90 | Employed NaOCN |
| | | 64,95 | 12,02 | 5,60 | |
| 10 | 92,1 | 63,51 | 11,08 | 5,92 | 150 ml DMF |
| | | 62,69 | 11,43 | 5,81 | |
| 11 | 99,0 | 44,42 | 9,46 | 19,92 | 150 ml DMF |
| | | 44,67 | 8,64 | 19,06 | |
| 12 | 84,8 | 48,68 | 9,46 | 5,97 | 150 ml DMF |
| | | 48,07 | 10,48 | 5,65 | |
| 13 | 88,0 | 48,56 | 9,72 | 13,07 | 150 ml DMF |
| | | 47,98 | 10,15 | 12,99 | |
| 14 | 99,5 | 32,86 | 5,24 | 19,16 | 40 ml DMF |
| | | 32,05 | 6,17 | 19,39 | |
| 15 | 98,4 | 57,41 | 10,71 | 7,44 | 200 ml DMF |
| | | 57,06 | 11,96 | 7,19 | |
| 16 | 93,8 | 51,62 | 8,66 | 9,26 | Solvent: DMSO |
| | | 51,07 | 9,17 | 9,17 | |
| 17 | 99,5 | 43,98 | 6,71 | 18,65 | 150 ml DMF |
| | | 42,69 | 6,43 | 17,95 | |
| 18 | 93,6 | 49,96 | 9,58 | 4,16 | 150 ml DMF |
| | | 49,75 | 9,93 | 3,94 | |
| 19 | 97,6 | 53,82 | 7,74 | 8,96 | 250 ml DMF |
| | | 52,85 | 7,68 | 8,87 | |
| 20 | 83,5 | 58,58 | 6,98 | 10,78 | 500 ml DMF |
| | | 56,40 | 7,10 | — | |
| 21 | 90,1 | 56,17 | 6,93 | 11,56 | 150 ml DMF |
| | | 55,76 | 6,69 | 11,03 | |
| 22 | 88,5 | 48,14 | 7,07 | 14,03 | 150 ml DMF |
| | | 46,75 | 7,04 | 13,42 | |
| 23 | 95,6 | 49,66 | 7,05 | 8,91 | 150 ml DMF |
| | | 49,50 | 6,82 | 8,58 | |
| 24 | 87,6 | 47,25 | 6,71 | 8,47 | 150 ml DMF |
| | | 48,08 | 7,92 | 8,12 | |
| 25 | 93,9 | 51,20 | 7,36 | 8,53 | 150 ml DMF |
| | | 50,41 | 7,37 | 8,66 | |
| 26 | 80,6 | 45,47 | 6,16 | 12,24 | 150 ml DMF |
| | | 45,43 | 6,42 | 11,46 | |
| 27 | 98,7 | 63,39 | 8,29 | 8,87 | 150 ml DMF |
| | | 63,56 | 8,30 | 8,73 | |
| 28 | 82,7 | 60,94 | 7,00 | 7,48 | 150 ml DMF |
| | | 60,11 | 7,87 | 7,70 | |
| 29 | 97,6 | 65,06 | 6,64 | 6,60 | 200 ml DMF |
| | | 64,98 | 6,63 | 6,51 | |
| 30 | 95,9 | 45,18 | 8,27 | 9,58 | 200 ml DMF |
| | | 45,28 | 8,91 | 9,84 | |
| 31 | 72,4 | 45,34 | 8,65 | 14,42 | 175 ml DMF |
| | | 45,05 | 9,18 | — | |
| 32 | 91,8 | 48,13 | 6,21 | 17,27 | 400 ml DMF |
| | | 49,62 | 6,98 | 17,15 | |
| 33 | 99,0 | 51,99 | 6,54 | 12,99 | 150 ml DMF |
| | | 50,31 | 6,88 | 12,11 | |
| 34 | 90,4 | 55,88 | 6,88 | 8,69 | 150 ml DMF |
| | | 56,41 | 7,13 | 8,45 | |
| 35 | 96,8 | 56,41 | 5,98 | 6,92 | 200 ml DMF |
| | | 56,05 | 6,08 | 6,81 | |
| 36 | 75,0 | 49,11 | 6,47 | 8,18 | 250 ml DMF |
| | | 48,44 | 6,69 | 7,76 | |

In the working examples, there were employed potassium cyanate and dimethylformamide unless otherwise indicated.

The new silylureas can be used as adhesives and for coating glass fibers in the same manner as the prior art compounds mentioned above.

What is claimed is:

1. A N,N' or N,N',N'-substituted silylurea of the formula (I)

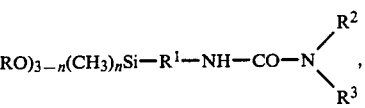

where
n is 0 or 1
R is $C_1$-$C_6$ alkyl, phenyl, $C_5$-$C_8$ cycloalkyl
$R^1$ is —$(CH_2)_3$—,

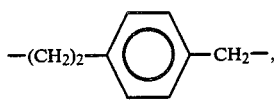

$R^2$, $R^3$ are
$C_1$-$C_3$ alkyl, terminally substituted by an amino-, thio- or cyano group,
—$(C_2H_4NH)_mH$ where m is 2 or 3,
$C_3$-$C_{18}$ alkenyl,

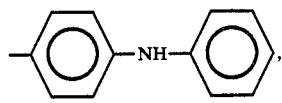

benzyl, pyridyl, triazyl or such a group having at least one substituent which is an amino, hydroxyl, thio, $C_1$-$C_3$ alkoxy, nitro, or carboxyl group or a silyl group, $R^2$ and $R^3$ together with the nitrogen atom and 0, 1, or 2 further heteroatoms forms a monovalent 5 to 14 numbered saturated or unsaturated cyclic group having 2 to 12 carbon atoms, with the proviso that $R^2$ can also be hydrogen, $C_1$-$C_{18}$ alkyl or $C_3$-$C_{18}$ alkenyl.

2. A silylurea according to claim 1 wherein $R^1$ is

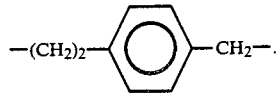

3. A silylurea according to claim 1 wherein at least one of $R^2$ and $R^3$ is alkenyl.

4. A silylurea according to claim 1 where

form an imidazole, pyrazole, 1,2,3-triazole, 1,2,4-triazole, piperazine, pyrazoline, imidazolidine, morpholine, thiazolidine, indazole, azimidobenzene, benzimidazole, indole, or phenothiazine ring.

5. A silylurea according to claim 1 wherein $R^2$ is a $C_1$-$C_3$ alkyl group having an amino, thio, or cyano group.

6. A silylurea according to claim 1 where R is $C_1$-$C_3$ alkyl and n is 0.

7. A silylurea according to claim 6 wherein $R^2$ is alkyl of 8 to 18 carbon atoms.

8. A process of producing a compound of the formula (I)

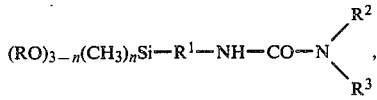

where n is 0 or 1

R is $C_1$-$C_6$ alkyl, phenyl, $C_5$-$C_8$ cycloalkyl $R^1$ is —$(CH_2)_3$—,

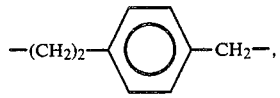

$R^2$, $R^3$ are $C_1$-$C_{18}$ alkyl, $C_5$-$C_8$ cycloalkyl, $C_1$-$C_3$ alkyl, terminally substituted by an amino-, thio- or cyano group, —$(C_2H_4NH)_mH$ where m is 2 or 3, $C_3$-$C_{18}$ alkenyl,

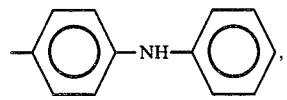

benzyl, phenyl, naphthyl, pyridyl, triazyl or such a group having at least one substituent which is an amino, hydroxyl, thio, $C_1$-$C_3$ alkoxy, nitro, or carboxyl group or a silyl group of the formula

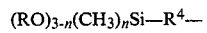
$(RO)_{3-n}(CH_3)_nSi$—$R^4$— in which $R^4$ is $C_1$-$C_3$ alkylene,

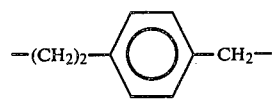

or $R^2$ and $R^3$ together with the nitrogen atom and 0, 1, or 2 further heteroatoms forms a monovalent 5 to 14 numbered saturated or unsaturated cyclic group having 2 to 12 carbon atoms, with the proviso that $R^2$ can also be hydrogen comprising first adding to a solution of an amino compound of the formula (III)

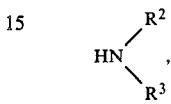

in an aprotic, polar, organic solvent an equimolar amount of alkali cyanate and subsequently adding an equimolar amount of a halosilane of the formula IV

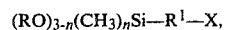
$(RO)_{3-n}(CH_3)_nSi$—$R^1$—X, where R, $R^1$ and n are as defined above and X=Cl, Br, or I, heating to 120° to 155° C., stirring for 1 to 8 hours at 130° to 150° C., and separating the product after the reaction.

9. A process according to claim 8 wherein the reaction is carried out at 140° C. for 4 hours.

10. A process according to claim 8 wherein 0.75 mole of trismethoxysilyl-3-chloropropane is reacted with 0.75 mole of ethylenediamine and 0.75 mole of potassium cyanate in 200 ml of dimethylformamide at 140° C. for 4 hours.

11. A process according to claim 8 wherein the solvent is dimethylformamide or dimethylsulfoxide.

12. A compound according to claim 1 wherein $R^2$ is hydrogen or $C_1$-$C_{18}$ alkyl.

13. A compound according to claim 1 having the formula:

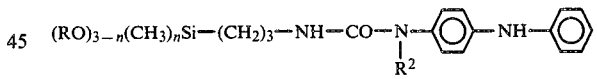

where $R^2$ is H or $C_1$-$C_{18}$-alkyl.

14. A compound according to claim 13 wherein $R^2$ is hydrogen.

15. A compound according to claim 13 wherein $R^2$ is $C_1$-$C_{18}$-alkyl.

* * * * *